(12) United States Patent
Komppa

(10) Patent No.: US 6,643,022 B1
(45) Date of Patent: Nov. 4, 2003

(54) METHOD AND DEVICE FOR DETERMINING FIBRE ORIENTATION IN A PAPER SAMPLE

(75) Inventor: Antero Komppa, Espoo (FI)

(73) Assignee: Ambertec Oy, Espoo (FI)

( * ) Notice: Subject to any disclaimer, the term of this patent is extended or adjusted under 35 U.S.C. 154(b) by 0 days.

(21) Appl. No.: 09/720,624

(22) PCT Filed: Jun. 21, 1999

(86) PCT No.: PCT/FI99/00544

§ 371 (c)(1),
(2), (4) Date: Feb. 22, 2001

(87) PCT Pub. No.: WO99/67625

PCT Pub. Date: Dec. 29, 1999

(30) Foreign Application Priority Data

Jun. 23, 1998 (FI) .................................................. 981443

(51) Int. Cl.[7] ........................ G01N 21/55; G01N 21/47; G01N 21/84
(52) U.S. Cl. ........................ 356/445; 356/446; 356/429
(58) Field of Search ................................ 356/445, 446, 356/429

(56) References Cited

U.S. PATENT DOCUMENTS

| 5,394,247 A | 2/1995 | Vahey et al. |
| 5,474,233 A | 12/1995 | Fukuoka et al. |
| 5,640,244 A | 6/1997 | Hellstrom et al. |

FOREIGN PATENT DOCUMENTS

| DE | 41 20 749 | 2/1992 |
| GB | 2 312 506 | 9/1997 |

*Primary Examiner*—Frank G. Font
*Assistant Examiner*—Amanda Merlino
(74) *Attorney, Agent, or Firm*—Andrus, Sceales, Starke & Sawall, LLP

(57) ABSTRACT

The invention relates to a method and device for determining fiber orientation in a paper sample. The surface of the sample (1) is illuminated from an oblique angle (11) by means of more than one light source (2, 3). The illumination is rotated on the surface of the sample by electronically switching the light sources on and off in turn by means of a switch (12). The intensity of the light reflected from the surface of the sample is measured using at least one sensor (5) and, based on the measured light intensity and momentary direction of illumination, the fiber orientation in the sample is determined by means of a computing device (13)

27 Claims, 3 Drawing Sheets

METHOD AND DEVICE FOR DETERMINING FIBRE ORIENTATION IN A PAPER SAMPLE

CROSS REFERENCE TO RELATED APPLICATION

The present application is the U.S. national stage application of International Application PCT/FI99/00544, filed Jun. 21, 1999, which international application was published on Dec. 29, 1999 as International Publication WO 99/67625 in the English language. The International Application claims the priority of Finnish Patent Application 981443, filed Jun. 23, 1998.

BACKGROUND OF THE INVENTION

The present invention relates to a method as defined in the claims and to a device as defined in the claims for determining fiber orientation in a paper sample.

In this context 'paper sample' refers to web-like products, such as paper, cardboard or other paper industry products, manufactured from lignocellulose based materials.

'Fiber orientation' refers to the orientation of the fibers in a paper sample. The fibers are mostly oriented in the machine direction rather than in the transverse direction. In a paper sample, the degree and angle of fiber orientation vary in relation to the web width, i.e. in the transverse direction of the paper web, and in relation to time, i.e. in the longitudinal direction of the paper web. Fiber orientation is generally different in different paper sorts.

Previously known is a method for determining the mean fiber orientation in a paper sample as a ratio of machine direction tensile strength to transverse direction tensile strength, i.e. as a strength ratio. Further, a method for determining mean orientation by measuring the speed of propagation of ultrasound in a web in different directions is known. In this method, the distance lag or sound modular ratio obtained indicates the mean orientation angle and degree. Devices suited for implementing the method are manufactured e.g. by Lorentzen & Wettre and Nomura.

Previously known is also a method for determining mean orientation by optical means. In the method, a thin round beam of light is directed at the paper surface and the shape of the beam is measured from the other side of the paper. The ellipticity of the shape of the beam increases in proportion to the degree of orientation in the sample. Instruments for this purpose are manufactured e.g. by Honeywell.

A problem with the prior-art methods is that only the mean fiber orientation in a certain area in the paper sample can be determined. Prior-art methods for determining fiber orientation are difficult to use in practice; for instance, the tensile strength ratio is not easy to determine. Tensile strength ratio is not a good measure of fiber orientation in other respect, either, because, in addition to fiber orientation, it depends on the drying history of the paper, such as the degree of shrinkage occurring in the web as it is drying.

A further problem is that prior-art methods are not applicable for the determination of surface orientation (surface orientation refers to fiber orientation at the paper surface) and surface orientation difference between surfaces.

However, determination of surface orientation is an important function because, depending on the former type used in the paper machine and on the grammage level of the paper web, the web may have a significant orientation difference between its surfaces. This is a problem especially in multi-layer type web formation, in which the layers of the web are produced using different head boxes/formers or a multi-channel head box. Moreover, a surface orientation difference can be clearly observed in paper produced using conventional head box—former combinations or dilution head boxes. For example, in fine grade paper and sheeted printing paper, a surface orientation difference and variations of orientation in different areas of the paper surface may cause severe curling of the sheet, which again may result in toppling of paper piles, among other things.

SUMMARY OF THE INVENTION

The object of the invention is to eliminate the problems mentioned above and to disclose a new workable method and device for determining fiber orientation that will be easier to implement in industrial applications. A further object of the invention is to disclose a method and device for determining, besides mean fiber orientation, fiber orientation separately for the upper and/or lower surfaces of a paper sample.

The method and device of the invention are characterized by what is presented in the claims.

The invention is based on determining fiber orientation in a paper sample.

According to the invention, the surface of the sample is illuminated from an oblique angle using more than one light source. The illumination is rotated on the surface of the sample by switching the light sources electronically on and off in turn by means of a switch. The intensity of the light reflected from the sample surface is measured by means of at least one sensor and, based on the measured light intensity and momentary direction of illumination, fiber orientation in the sample is determined using a computing device.

Based on the measured light intensity and the momentary direction of illumination, it is possible to determine the directional angle and/or degree of fiber orientation in the sample. The surface of the sample can be illuminated and/or the intensity of the light reflected from the sample surface can be measured continuously.

In an embodiment of the invention, the surface of the sample is illuminated using LED type light sources. If desirable, the sample can be illuminated with polarized or non-polarized light.

In an embodiment of the invention, the intensity of the light reflected from the surface of the sample is measured using a light emitting diode. The light emitting diode is disposed e.g. substantially perpendicularly to the sample surface. In an embodiment, at least two sensors are disposed substantially in the form of a bar, and the bar is placed in a position substantially perpendicular to the direction of motion of the sample.

In an embodiment of the invention, the light sources and sensor are disposed in a substantially unitary assembly, forming a measuring device. In an embodiment, the device comprises a movable controlling element, the measuring device being placed substantially in conjunction with said controlling element. The measuring device as such may be free of movable parts. The controlling element may be designed to be movable by a previously known technique, e.g. using a hydraulic device.

According to an embodiment, the measurement is performed substantially above and below the sample. In an embodiment of the invention, the sample is a moving web.

With the method and/or device of the invention, fiber orientation on different surfaces of the sample can be determined separately so that it will be possible to determine separate surface orientations and a surface orientation difference in addition to the mean fiber orientation. A further advantage of the invention is that it allows on-line type determination of fiber orientation even from a moving sample and without breaking the sample.

A further advantage is an insignificant need for maintenance of the measuring device because the measuring device is completely or partially free of movable parts. A further advantage is a compact size and simplicity of manufacture of the device. The apparatus can be easily added to existing equipment e.g. in paper industry without any substantial changes, thus allowing easy, quick and advantageous implementation of the method.

A further advantage of the invention is reproducibility and stability of the light intensity measured by the sensor.

BRIEF DESCRIPTION OF THE SEVERAL VIEWS OF THE DRAWING

In the following, the invention will be described by the aid of detailed examples of its embodiments with reference to the attached drawings, wherein.

DETAILED DESCRIPTION OF THE INVENTION

Figure 1:
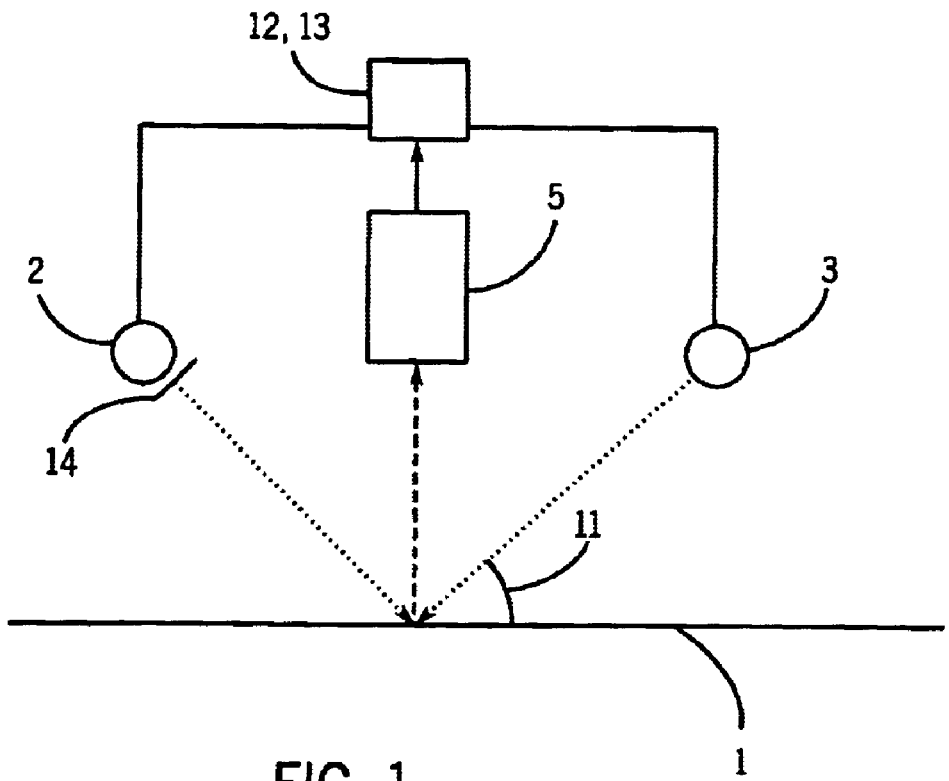
FIG. 1 presents an embodiment of the device of the invention in lateral view.

FIG. 1 presents an embodiment of the apparatus of the invention for the measurement of fiber orientation. In this embodiment, LED-type light sources 2 and 3 are used. LED-type light sources can be turned on and off very rapidly without substantial delays. The number of light sources is more than one, preferably at least three.

FIG. 1 shows further that the light sources illuminate the surface of the sample 1 from an oblique angle 11 of e.g. about 45 degrees. It is naturally possible to illuminate the sample surface from angles of other sizes as well. The illuminating beam may typically have a small diameter, e.g. below 10 mm.

The sample in this embodiment is a moving paper web, from whose surface the light is reflected substantially perpendicularly in an upward direction. The angle of incidence of the light on the paper surface and the angle of departure of the reflected light from the surface may differ from each other; for instance, the ratio of incidence angle to departure angle is 45°/90°. The intensity of the light reflected from the surface is measured using at least one sensor 5, which in the embodiment in FIG. 1 is a light emitting diode, preferably disposed perpendicularly to the sample. The measurement is performed in a measuring area having a diameter below 10 mm.

The surface of the sample 1 can be illuminated and/or the intensity of the light reflected from the sample surface can be measured continuously.

Figure 2:
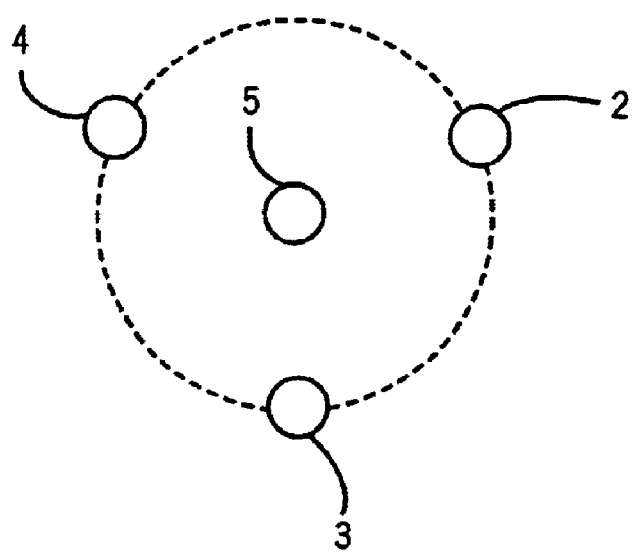
FIGS. 2 and 3 present embodiments of devices according to the invention in top view.
Figure 3:
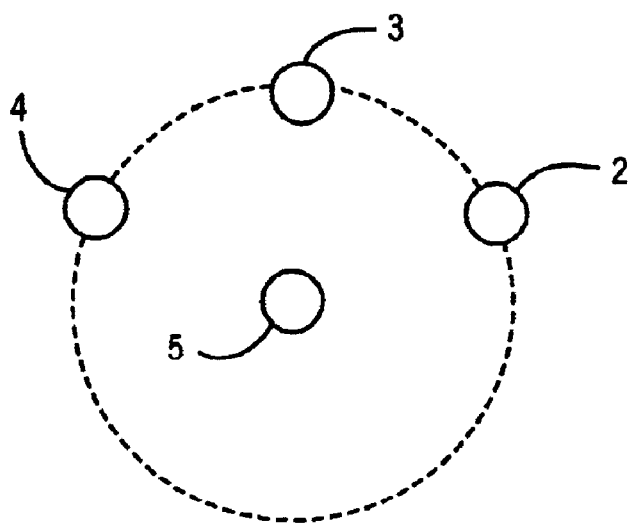

FIG. 2 presents an embodiment of the disposition of the light sources 2, 3 and 4 in relation to the sensor 5 as seen from above. The light sources can be placed at equal distances in a circular arrangement on the circumference of an imaginary circle e.g. so that the sensor remains at the centre of the light sources in the middle of the circle. In a preferred case, the light sources can also be disposed in a semicircular arrangement on the circumference of an imaginary circle, e.g. as illustrated in FIG. 3, while the sensor is placed at the centre of the imaginary circle.

The illumination is rotated on the surface of the sample by turning the light sources on and off successively by means of an electronic switch 12 (FIG. 1). Since the turn-on time of especially LED-type light sources is very short, a high virtual speed of rotation is achieved without movable parts as light rays proceeding from different directions, i.e. light sources, are turned on and off and the illumination substantially rotates around the spot on the sample surface observed by the sensor. In the device of the invention, it is possible to use any LED-type light sources and electronic switches known in this field, the details of which will not be described in this context.

As the light beam is rotated, the light falls on the sample surface from different directions, so it is reflected from the sample surface in different ways depending on the fiber orientation and the direction of the light directed at the fibers. Maximum reflection occurs when the light falls on the fiber perpendicularly from a lateral direction.

In the embodiment in this example, the intensity of the light reflected from the illuminated spot on the surface of a sample to which an illuminating beam is applied alternately from three directions is measured. On the basis of the measurement or series of measurements of light intensity and the momentary direction of illumination, it is possible to determine the directional angle and/or degree of fiber/surface orientation. The determination of fiber/surface orientation can be performed on the basis of the measurement results by using a separate computing device, which may be any known computing device 13 (FIG. 1) which will not be described here in detail.

To produce polarized light, a polarizing element 14 (FIG. 1), e.g. a polarization filter, may be placed in front of each LED-type light source 2 and 3. Other solutions for producing polarized light, such as a light source producing polarized light directly, can also be utilized in the method. Naturally, nonpolarized light may be used as well.

Figure 4:
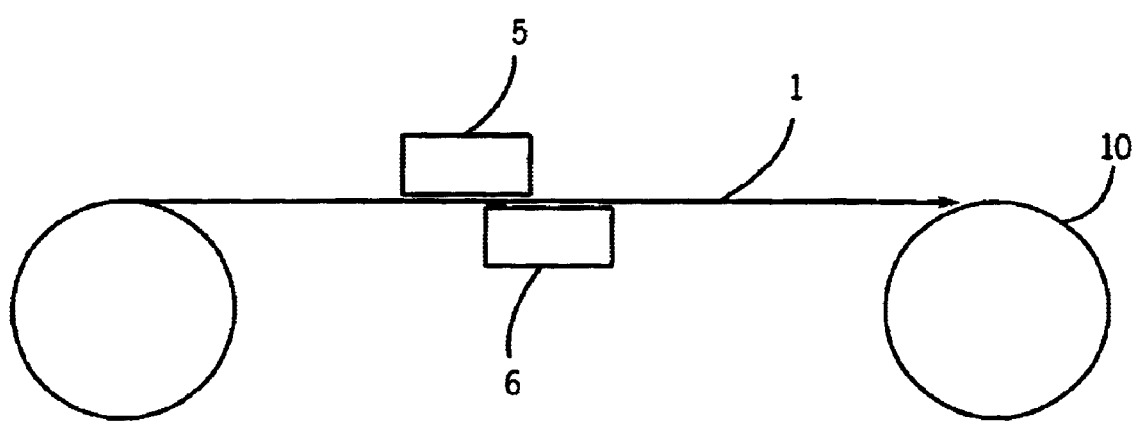
FIG. 4 presents an embodiment of a device according to the invention.

FIG. 4 presents an embodiment of the device of the invention. In this embodiment, the sensors 5 and 6 are mounted in pairs above and below the paper sample 1, the first one 5 of the sensors being placed above the paper sample and the second one 6 above it. The sensors are placed against the paper web 1 so that opposite sensors also form a support for the paper web during the measurement, preventing the sample from fluttering in the measuring gap. The sensors measure the surface orientation in both surfaces simultaneously. The sensors above and below the sample can be disposed in a stepped manner relative to each other in the direction of motion of the sample as shown in the figure, so that light rays penetrating the paper will not disturb the measurement.

Figure 5:
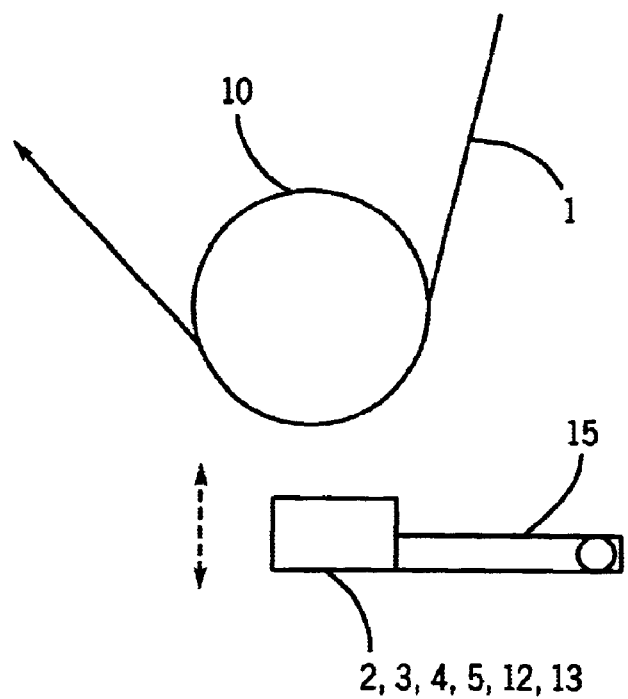
FIG. 5 presents an on-line embodiment of a device according to the invention.

FIG. 5 shows an on-line embodiment of the device of the invention. The measuring device is mounted substantially in conjunction with a movable controlling element 15. In this embodiment, the sensor 5, light sources 2, 3 and 4, electronic switch 12 and computing device 13 form a substantially unitary measuring device. The measuring device may naturally only consist of a sensor and/or light sources.

The measuring device in itself is preferably free of movable parts, thus reducing the need for maintenance.

In the embodiment in FIG. 5, the controlling element 15, held in a measuring position, is brought close to the paper sample 1, which is moving e.g. on a rigid cylinder 10 with a large diameter in a paper machine. In this embodiment, the measuring device does not come into contact with the sample. The controlling element can be moved, in this embodiment raised and lowered as necessary. The on-line embodiment of the device can be used to measure light intensity from a moving paper sample, such as a web running in the wire section of a paper machine.

Figure 6:
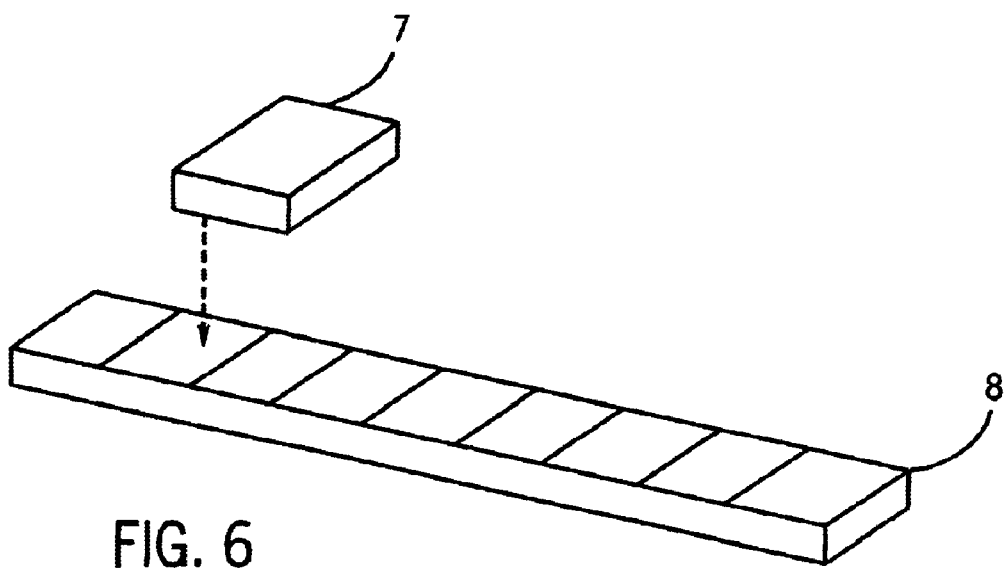
FIG. 6 presents a detail of the embodiment presented in FIG. 5.

FIG. 6 presents a detail of FIG. 5. In the embodiment in FIG. 6, instead of a single sensor 5, a sensor bar 8, i.e. a measuring device consisting of a number of sensor modules 7, i.e. sensors mounted side by side, is connected to a controlling element 15. The sensor bar is so mounted on the controlling element that the bar is substantially perpendicular to the direction of motion of the sample 1. In this embodiment, the size of the sensor modules may be e.g. 50×100 mm. A sensor bar with sensor modules mounted on it can be used for continuous measurement of surface orientation profile across the whole width of a paper web, e.g. with a spacing of 50 mm, for instance to implement accurate monitoring of the effects of adjustments of the headbox lip of the paper machine.

Each sensor module 7 may naturally comprise light sources, an electronic switch and/or a computing device besides a sensor or sensors. Alternatively, for each sensor or sensor module on the bar, the sensor bar 8 may naturally be provided with a given number of light sources and other components of the device of the invention. Several sensor bars may be used in conjunction with the device of the invention.

In the embodiment in FIG. 5, the intensity of the light reflected from the surface of the paper is measured from both sides of the web 1 using two controlling elements 15 disposed on either side of the web, e.g. substantially in the vicinity of two successive rollers or cylinders so that the first controlling element is above the web and the second one below it.

Results obtained using the method and device of the invention for determining fiber orientation have been compared with fiber orientations determined using a commercial sound module measuring device. The results obtained indicate that the method of the invention and the previously known method of determination correspond to each other.

Furthermore, reproducibility measurements performed on exactly the same spot have proved that the light intensity measured using a sensor according to the invention is reproducible and stable.

The method and device of the invention are applicable as different embodiments for the determination of any fiber orientation, especially surface orientation in a paper web.

The embodiments of the invention may be varied within the scope of the following claims.

What is claimed is:

1. A method for determining fiber orientation in a paper sample comprising the steps of:

providing a light sensor, the light sensor being spaced from the sample and facing a surface of the sample to receive light from an area on the surface of the sample viewed by the light sensor;

arranging a plurality of light sources in circumferentially spaced positions at least partially around the light sensor, the light sources being radially spaced from the light sensor and being spaced from the sample;

successively turning each of the light sources on and then off to cause each of the light sources, in turn, to sequentially and obliquely project a beam of light from the light source onto the area on the sample, the arcuate spacing of the light sources causing the light beam of each of the sources to illuminate the area from a different direction, the successive turning on and off of the light sources being at a common frequency in which a given light source is on while the other light sources are off and off while other light sources are on, the successive, repetitive turning on and off of the light sources at the common frequency creating a rotational effect in the illumination of the area of the sample;

receiving, with the light sensor, a series of light signals comprising light obtained from the sample as a result of the sequential illumination of the area on the sample from different directions by the light projected from the light sources, the properties of the obtained light signals being dependent on the orientation of fibers in the sample and the direction of illumination of the sample by each of the light sources;

measuring a property of each of the received light signals;

using the properties of the received light signals and the associated directions of illumination to determine fiber orientation properties of the sample.

2. Method as defined in claim 1, characterized in that, in the method, at least one of the directional angle and degree of fiber orientation in the sample is determined.

3. Method as defined in claim 1, characterized in that the surface of the sample is illuminated using LED-type light sources.

4. Method as defined in claim 1, characterized in that the surface of the sample is illuminated substantially at an angle of about 45 degrees.

5. Method as defined in claim 1, characterized in that the surface of the sample is illuminated by means of three light sources.

6. Method as defined in claim 1, characterized in that the light sources are disposed in a circular arrangement and surround the light sensor.

7. Method as defined in claim 1, characterized in that the light sources are disposed in a semicircular arrangement and partially surround the light sensor.

8. Method as defined in claim 1, characterized in that the sample is illuminated with polarized light.

9. Method as defined in claim 1, characterized in that the light obtained from the surface of the sample is sensed by means of a light emitting diode.

10. Method as defined in claim 1, characterized in that the sensor is disposed in a substantially perpendicular position relative to the surface of the sample.

11. Method as defined in claim 1, characterized in that the paper sample is a moving web.

12. A device for determining fiber orientation in a paper sample comprising:

a light sensor spaced from the sample and facing a surface of the sample to receive light from an area on the surface of the sample viewed by said light sensor;

a plurality of light sources located in circumferentially spaced positions at least partially around said light sensor, said light sources being radially spaced from said light sensor and being spaced from the sample;

means for electronically, successively switching each of said light sources on and then off to cause each of said light sources, in turn, to sequentially and obliquely project a beam of light from the light source onto the area on the sample, the arcuate spacing of said light sources causing the light beam of each of said sources to illuminate the area from a different direction, the successive switching on and off of said light sources being at a common frequency in which a given light source is on while the other light sources are off and off while other light sources are on, the successive, repetitive switching on and off of said light sources at the common frequency creating a rotational effect in the illumination of the area of the sample;

said light sensor receiving a series of light signals comprising light obtained from the sample as a result of the sequential illumination of the area on the sample from different directions by the light projected from said light sources, the properties of the obtained light signals being dependent on the orientation of fibers in the sample and the direction of illumination of the sample by each of said light sources; and means coupled to said light sensor for determining fiber orientation properties of the sample from the properties of the received light signals and the associated directions of illumination.

13. Device as defined in claim 12, characterized in that the light sources are LED-type light sources.

14. Device as defined in claim 12, characterized in that the angle (11) of illumination of the light sources is substantially about 45 degrees.

15. Device as defined in claim 12, characterized in that the device comprises three light sources.

16. Device as defined in claim 12, characterized in that the light sources are disposed in a circular arrangement and surround said light sensor.

17. Device as defined in claim 12, characterized in that the light sources are disposed in a semicircular arrangement and partially surround said light sensor.

18. Device as defined in claim 12, characterized in that the device comprises a polarizing element disposed substantially in conjunction with at least one of the light sources.

19. Device as defined in claim 12, characterized in that said light sensor is a light emitting diode.

20. Device as defined in claim 12, characterized in that the device comprises at least two devices disposed substantially side by side in the form of a bar.

21. Device as defined in claim 12, characterized in that the light sources and said light sensor are disposed in a substantially unitary assembly forming a device so that the light sensor is substantially perpendicular to the surface of the sample.

22. Device as defined in claim 12, characterized as including a movable controlling element (15), the device for determining fiber orientation being disposed substantially in conjunction with said controlling element.

23. Device as defined in claim 12, characterized in that the device is substantially free of movable parts.

24. Device as defined in claim 12, characterized in that the device is a continuously operating device.

25. Method as defined in claim 1 characterized in that at least one of the step of successively turning the light sources on and off and the step of receiving the light signals is carried out continuously.

26. Method as defined in claim 11 characterized as carrying out the steps of the method at a plurality of locations arranged in a direction transverse to the direction of movement of the web.

27. Method as defined in claim 1 wherein the paper sample has a pair of surfaces and wherein the steps of the method are carried out for both surfaces of the paper sample.

* * * * *